(12) United States Patent
Zhou et al.

(10) Patent No.: US 7,981,939 B2
(45) Date of Patent: Jul. 19, 2011

(54) APPLICATION OF 2-BROMIDE-ISOVANILLIN FOR THE MANUFACTURE OF A MEDICAMENT FOR ANTI-CANCER OR/AND RADIATION/CHEMOTHERAPY SENSITIZATION

(75) Inventors: Pingkun Zhou, Beijing (CN); Yuqian Yan, Beijing (CN); Lin Wang, Beijing (CN); Jianli Sui, Beijing (CN)

(73) Assignee: Institute of Radiation Medicine, Academy of Military Medical Sciences, PLA, Beijing (CN)

( * ) Notice: Subject to any disclaimer, the term of this patent is extended or adjusted under 35 U.S.C. 154(b) by 297 days.

(21) Appl. No.: 12/072,496

(22) Filed: Feb. 25, 2008

(65) Prior Publication Data
US 2011/0098362 A9 Apr. 28, 2011

Related U.S. Application Data

(63) Continuation of application No. PCT/CN2006/002191, filed on Aug. 25, 2006.

(30) Foreign Application Priority Data

Aug. 25, 2005 (CN) .......................... 2005 1 0093043

(51) Int. Cl.
*A61K 31/11* (2006.01)
*A01N 35/00* (2006.01)
(52) U.S. Cl. ...................................................... 514/699
(58) Field of Classification Search .................. None
See application file for complete search history.

(56) References Cited

U.S. PATENT DOCUMENTS

| 6,812,258 B2 | 11/2004 | Bessette et al. |
| 7,008,649 B2 | 3/2006 | Bessette et al. |
| 2002/0182268 A1 | 12/2002 | Bessette et al. |
| 2003/0017218 A1 | 1/2003 | Bessette et al. |
| 2004/0146595 A1 | 7/2004 | Bessette et al. |

FOREIGN PATENT DOCUMENTS

| CN | 1154355 A | 7/1997 |
| CN | 1329498 A | 1/2002 |
| EP | 0758639 A1 | 2/1997 |

OTHER PUBLICATIONS

Trost et al. Divergent enantioselective synthesis of (–)-galanthamine and (–)-morphine. J. Am. Chem. Soc. 2005, 127, 14785-14803.*
Univar. Excipients/Processing Aids. Mar. 1, 2005.*
Zhenshun et al., "The Synthetic Methods and Usage of Vanillin", China Food Additives, No. 6, pp. 101-106, 2004.
Durant et al., "Vanillins-a Novel Family of DNA-PK Inhibitors", Nucleic Acids Research, vol. 31, No. 19, pp. 5501-5512, 2003.
Tsuda et al., "Chemopreventive Effects of β-Carotene, α-Tocopherol and Five Naturally Occurring Antioxidants on Initiatoin of Hepatocarcinogenesis by 2-Amino-3-methylimidazo[4,5-*f*]quinoline in the Rat", Jpn. J. Cancer Res., 85, pp. 1214-1219, 1994.
International Search Report from PCT/CN2006/002191.

* cited by examiner

*Primary Examiner* — Brandon J Fetterolf
*Assistant Examiner* — Anna Pagonakis
(74) *Attorney, Agent, or Firm* — Venable LLP; Michael A. Sartori; Michael E. Nelson

(57) ABSTRACT

Use of 2-bromo-isovanillin in the preparation of an anticancer medicament and/or radio- and chemotherapy sensitizing medicament is disclosed. The medicament for the treatment of cancers and/or for radio- and chemotherapy sensitization comprising 2-bromo-isovanillin as active ingredient provided herein has the following features: (1) low toxicity, without evident adverse effects; (2) significant therapeutic effect, with remarkable proliferation inhibiting and pro-apoptotic effects in tumor cells; (3) a broad-spectrum anticancer activity; (4) suitable to be used in combination with antimetabolites, to enhance the effects and meanwhile lower the toxicity, and also to reduce multi-drug resistance; (5) convenient and safe administration, the main route being oral.

2 Claims, 6 Drawing Sheets
(4 of 6 Drawing Sheet(s) Filed in Color)

0 μM                    2-bromo-isvanillin 40 μM   24 h

APPLICATION OF 2-BROMIDE-ISOVANILLIN FOR THE MANUFACTURE OF A MEDICAMENT FOR ANTI-CANCER OR/AND RADIATION/CHEMOTHERAPY SENSITIZATION

This application is a Continuation of International Application PCT/CN2006/002191, filed Aug. 25, 2006, which claims priority to foreign application CN200510093043.X, filed Aug. 25, 2005.

TECHNICAL FIELD

The present invention relates to a new use of a compound, in particular to use of 2-bromo-isovanillin, a derivative of vanillin, in the preparation of an anticancer medicament and/or radio- and chemotherapy sensitizing medicament.

BACKGROUND ART

Malignant tumor is one of those diseases that seriously endanger human health. Currently, no effective treatment or prophylaxis is yet available. Thus, it is still the predominant task in the treatment of tumor to search for an effective preventive and/or therapeutic agent.

Vanillin compounds have aromatic odor, exhibit inhibition of bacterial growth and refreshing effect, and thus have been widely used as a food additive. Studies showed that vanillins, at a certain concentration, could also inhibit the activity of DNA repairing proteins DNA-PKcs and the invasion of cancer cells (Durant S and Karran P. Vanillins—a novel family of DNA-PK inhibitors. Nucleic Acids Research, 2003, 31(19): 5501-5512; Tsuda H, Uehara N, Iwahori Y, Asamoto M, Iigo M, Nagao M, Matsumoto K, Ito M and Hirono I. Chemopreventive effects of beta-carotene, alpha-tocopherol and five naturally occurring antioxidants on initiation of hepatocarcinogenesis by 2-amino-3-methylimidazo[4,5-f]quinoline in the rat. Jpn J. Cancer Res., 1994, 85: 1214-1219). Derivatives of vanillin include ethyl vanillin (molecular structure as shown in formula 1), 4-methoxyvanillin (molecular structure as shown in formula 2), isovanillin (molecular structure as shown in formula 3) and 2-bromo-isovanillin (molecular structure as shown in formula 4, also known as 6-bromo-isovanillin), and etc.

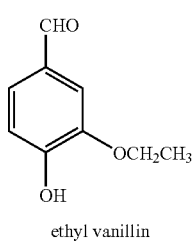

ethyl vanillin formula 1

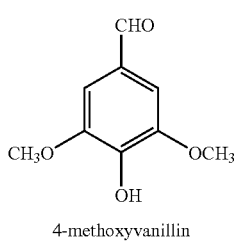

4-methoxyvanillin formula 2

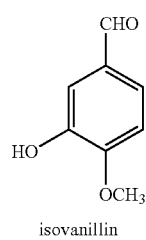

isovanillin formula 3

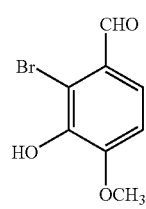

2-bromo-isovanillin formula 4

It is an effective approach in the development of new anti-cancer drugs to discover among various vanillin derivatives a compound having stronger activity of killing cancer cells and to identify the mechanism underlying the anticancer effect.

CONTENTS OF THE INVENTION

The study made by the present inventors showed that 2-bromo-isovanillin (2-bromo-3-hydroxy-4-methoxybenzaldehyde), a derivative of vanillin, has anticancer effect and/or radio- and chemotherapy sensitizing effect, and can be widely used in the preparation of an anticancer medicament and/or radio- and chemotherapy sensitizing medicament.

In the first aspect, the present invention relates to use of 2-bromo-isovanillin in the preparation of an anticancer medicament and/or radio- and chemotherapy sensitizing medicament. In specific embodiments, the medicament is in the form of capsules, tablets, powders, granules, oral solutions or injections.

In the second aspect, the present invention provides a pharmaceutical composition for the treatment of cancers and/or for radio- and chemotherapy sensitization, which comprises an effective amount of 2-bromo-isovanillin. In specific embodiments, the pharmaceutical composition is in the form of capsules, tablets, powders, granules, oral solutions or injections.

In the third aspect, the present invention provides a method for treating cancer and/or increasing the sensitivity to radio- and chemotherapy in a subject, which comprises administering to said subject an effective amount of 2-bromo-isovanillin. In specific embodiments, the method comprises administering 2-bromo-isovanillin in an amount of 5-10 mg per kg of body weight once every 2-3 days, for a period of 10-12 days; or once between 12 and 18 hrs prior to each radio/chemotherapy.

To the anticancer medicament comprising 2-bromo-isovanillin as active ingredient, if desired, one or more pharmaceutically acceptable adjuvants, including diluent, excipient, filler, binder, wetting agent, absorption enhancer, surfactant, lubricant, stabilizer and the like that are conventional in pharmaceutical field, may be added; if necessary, flavoring agent, sweetening agent, coloring agent and the like may also be added.

In addition to capsules, the anticancer medicament comprising 2-bromo-isovanillin as active ingredient may also be formulated in the form of tablets, powders, granules, oral solutions, injections and the like. The various dosage forms as mentioned above can be prepared according to routine methods in pharmaceutical field.

The amount to be used will typically range from 5 to 10 mg 2-bromo-isovanillin per kg of body weight, once every 2-3 days, for a period of 10-12 days; or once between 12 and 18 hrs prior to each radio/chemotherapy.

It has been experimentally proved that 2-bromo-isovanillin could inhibit proliferation of cancer cells, induce apoptosis in cancer cells, increase the sensitivity of tumor cells to radiation and chemotherapeutics, arrest cancer cells at G2/M phase, facilitate degradation of oncogene c-myc protein, and inhibit the activity of DNA repairing proteins DNA-PKcs, and its anticancer activity is significantly stronger than that of vanillin and other derivatives. The medicament for the treatment of cancers and/or for radio- and chemotherapy sensitization comprising 2-bromo-isovanillin as active ingredient provided herein has the following advantages: (1) low toxicity, without evident adverse effects; (2) significant therapeutic effect, with a remarkable inhibiting effect on the proliferation of tumor cells and a pro-apoptotic effect, tumor inhibition up to 80-95% upon administration for 6 consecutive days; (3) a broad-spectrum anticancer activity, with anticancer effects to different degrees in human malignant tumors of various origins, such as liver, lung, cervical, ovarian cancers, glioma and leukemia; (4) suitable to be used in combination with antimetabolites, to enhance the effects and meanwhile lower the toxicity, and also to reduce multi-drug resistance; (5) convenient and safe administration, both at home and in trip, the main route being oral. The above properties all contribute to the unique anticancer effect of 2-bromo-isovanillin, which promises wide application in medical field.

The present invention will be further described in detail with reference to the Examples.

DESCRIPTION OF THE FIGURES

The file of this patent contains at least one drawing executed in color. Copies of this patent with color drawings will be provided by the Office upon request and payment of the necessary fee.

MODE OF CARRYING OUT THE INVENTION

Unless specifically indicated, the methods used in the following examples are all conventional.

Cell Lines and Culture Conditions:

Human cervical cancer cell line HeLa, human liver cancer cell line HepG2/7221/7402, human ovarian cancer cell line HOC8/A2780, human glioma cell line BT325, lung cancer cell line A549, brain metastatic lung cancer cell line BT72 and normal human hepatic cell line LO2 were all grown in DMEM liquid medium supplemented with 10% newborn calf serum. Human leukemia cell line Jurkat was grown in 1640 medium supplemented with 10% newborn calf serum. The above cell lines were cultured in a $CO_2$ incubator at 5% $CO_2$ at 37° C.

Example 1

Figure 1A:
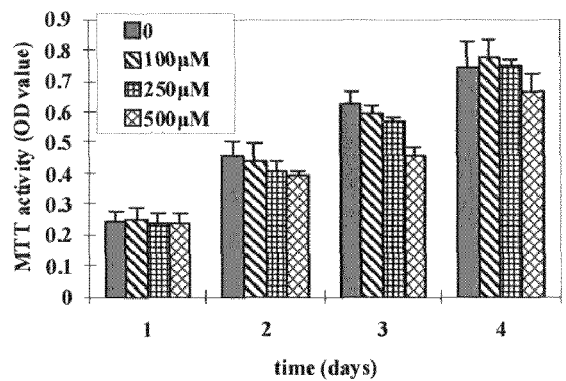
FIG. 1A shows the effect of vanillin on the proliferation of human cervical cancer cell line HeLa as measured by MTT assay.

Screening of Vanillin Derivatives Exhibiting a Remarkable Inhibitory Effect on the Proliferation of Cancer Cells 1. Effect of Vanillin on the Proliferation of Cancer Cells as Measured by MTT Assay By way of example, human cervical cancer cell line HeLa was used to study the effect of vanillin on the proliferation of cancer cells by MTT assay. Specifically, human cervical cancer cells HeLa were seeded into a 96-well plate at a density of $5 \times 10^3$ cells/well, and were divided into four groups. To each of the groups vanillin was added at a concentration of 0, 100, 250 or 500 μmol/L, respectively, and was allowed to grow for 4 days. Using the MTT assay, the optical density (OD) values at 490 nm were measured and recorded every day, wherein the OD value is indicative of the number of cells, i.e., the proliferation of cells. The results, as shown in FIG. 1A, indicated that vanillin effectively inhibited the proliferation of cancer cells at a concentration above 250 μmol/L.

2. Effect of Vanillin Derivatives for 72 Hrs on the Proliferation of Cancer Cells as Measured by MTT Assay By way of example, human cervical cancer cell line HeLa was used to study the effect of several vanillin derivatives for 72 hrs on the proliferation of cancer cells by MTT assay.

Figure 1B:
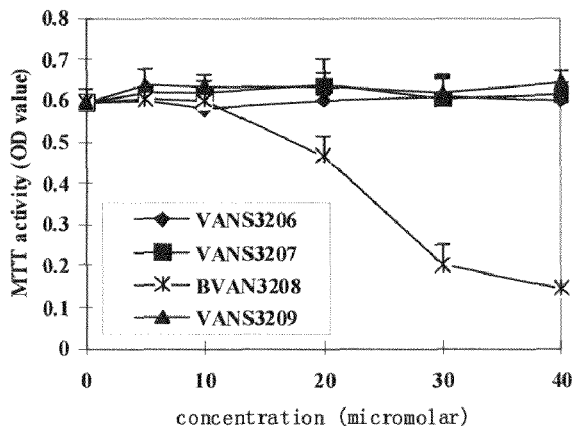
FIG. 1B shows the effect of treatment with vanillin derivatives for 72 hrs on the proliferation of human cervical cancer cell line HeLa as measured by MTT assay.

Specifically, human cervical cancer cells HeLa were seeded into a 96-well plate at a density of 5×10³ cells/well, and were divided into four groups. To each of the groups were added increasing concentrations (0, 10, 20, 30, 40 μmol/L) of vanillin derivatives ethyl vanillin (Code No. VAND3206), 4-methoxy vanillin (Code No. VAND3207), isovanillin (Code No. VAND3209) and 2-bromo-isovanillin (Code No. VAND3208), and the cells were cultured for 72 hrs. Using the MTT assay, the optical density (OD) values at 490 nm were measured and recorded every day, wherein the OD value is indicative of the number of cells, i.e., the proliferation of cells. The results, as shown in FIG. 1B, showed that ethyl vanillin, 4-methoxy vanillin and VAND3209 (isovanillin) had no inhibitory effect on the proliferation of HeLa cells at concentrations of less than 40 μmol/L up to 72 hrs, whereas 2-bromo-isovanillin (2-bromo-3-hydroxy-4-methoxybenzaldehyde) exhibited a significant inhibition of the proliferation of HeLa cells.

Figure 1C:
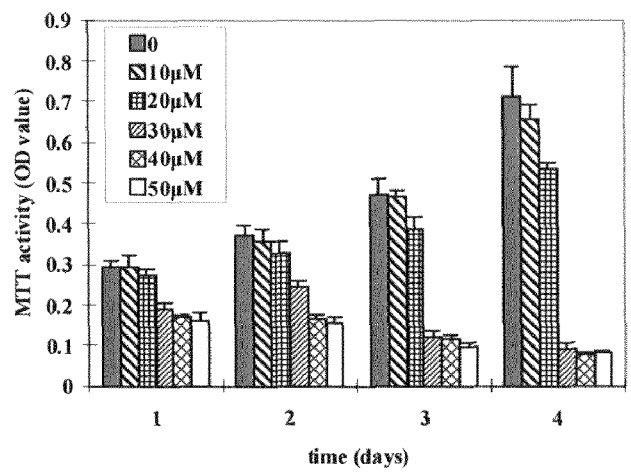
FIG. 1C shows the inhibitory effect of 2-bromo-isovanillin at different concentrations for various periods of time on the proliferation of human cervical cancer cell line HeLa as measured by MTT assay.

3. Inhibitory Effect of Different Concentrations of 2-Bromo-Isovanillin for Different Periods of Time on the Proliferation of Cancer Cells as Measured by MTT Assay By way of example, human cervical cancer cell line HeLa was used to study the inhibitory effect of 2-bromo-isovanillin at different concentrations for different periods of time on the proliferation of cancer cells by MTT assay. Specifically, human cervical cancer cells HeLa were seeded into a 96-well plate at a density of 5×10³ cells/well, and were divided into four groups. To each of the groups 2-bromo-isovanillin was added at a concentration of 0, 10, 20, 30, 40 or 50 μmol/L, and was cultured for 14 days, respectively. Using the MTT assay, the optical density (OD) values at 490 nm were measured and recorded every day, wherein the OD value is indicative of the number of cells, i.e., the proliferation of cells. The results, as shown in FIG. 1C, indicated that 2-bromo-isovanillin, at a concentration of 20 μmol/L, already had a remarkable inhibitory effect on the proliferation of HeLa cells, and at a concentration of 30 μmol/L or above for 4 days, the cancer cells completely lost their proliferative capabilities.

The above experimental results indicated that, as compared with vanillin and other vanillin derivatives, 2-bromo-isovanillin (2-bromo-3-hydroxy-4-methoxy benzaldehyde) significantly inhibited the proliferation of cancer cells.

Example 2

Figure 2:
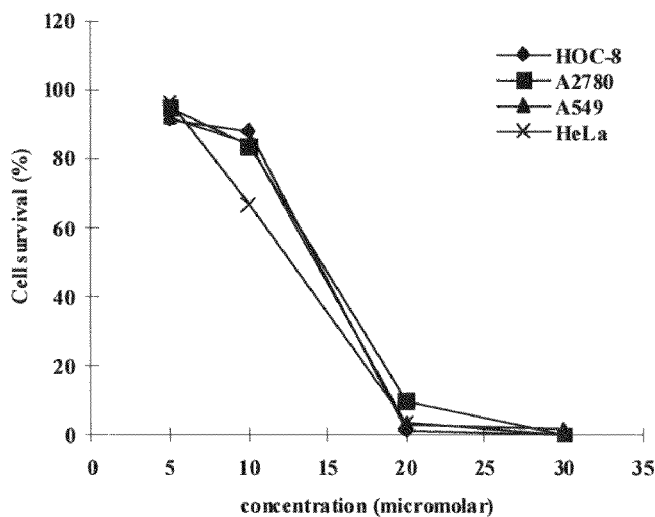
FIG. 2 shows the survival curves of a number of solid tumor cells under 6 days' continuous action of 2-bromo-isovanillin.

2-bromo-isovanillin Inhibited Proliferation and Induced Apoptosis in Cancer Cells The effect of 2-bromo-isovanillin in inhibiting proliferation and inducing apoptosis in solid tumor cells of different tissue origins was investigated by clonogenic assay as follows:

1. Determination of the Killing of Cancer Cells by 2-Bromo-Isovanillin for 6 Days By way of example, human cervical cancer cell line HeLa, lung cancer cell line A549, and ovarian cancer cell lines A2780 and HOC8 were used to determine the killing of cancer cells by 2-bromo-isovanillin for 6 days. Specifically, four groups were formed according to the type of the cancer cells. The cancer cells were diluted as appropriate, and were respectively plated into Petri dishes with a diameter of 60 cm, the amount of the cells adjusted depending on the concentration of 2-bromo-isovanillin to be added. Once adherence was achieved, each cell type received dosages of 0, 5, 10, 15, 20, 25, 30 and 35 μmol/L in triplicates. After 6 days of continuous action, the medium was replaced by a drug-free DMEM liquid medium. The cells were cultured for a total of 2 weeks. At the end of the culturing period, the cells were fixed and subjected to Giemsa staining. Then the cell clones were counted. The experimental data were expressed as the mean of 2-4 experiments and were plotted as a growth curve of cancer cells. As shown in FIG. 2, at 20 μmol/L of 2-bromo-isovanillin, the survival rates of human cervical cancer cells HeLa, lung cancer cells A549, and ovarian cancer cells A2780 and HOC8 were all lower than 10%, and at 30 μmol/L of 2-bromo-isovanillin, the proliferation of all four cancer cells were completely inhibited, resulting in cell death.

Figure 3:
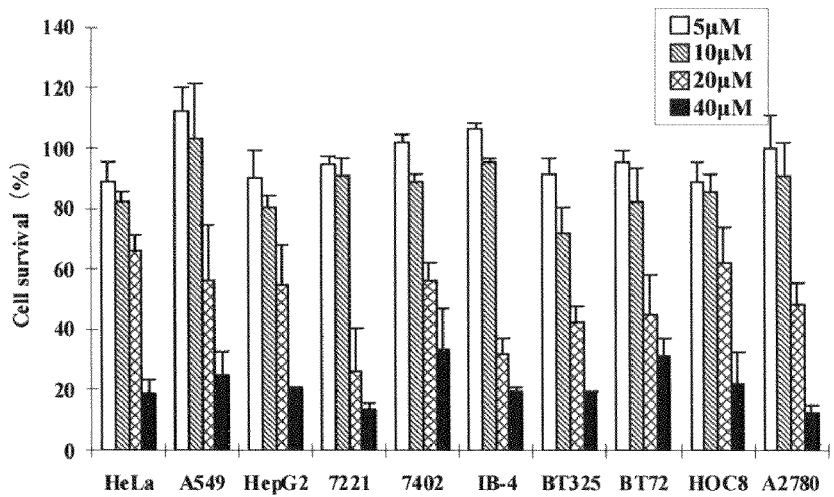
FIG. 3 shows the survival curves of a number of solid tumor cells under 24 hrs' continuous action of 2-bromo-isovanillin.

2. Determination of the Killing of Cancer Cells by 2-Bromo-Isovanillin for 24 Hrs By way of example, human cervical cancer cell line HeLa, human liver cancer cell lines HepG2/7221/7402, human ovarian cancer cell lines HOC8/A2780, human glioma cell line BT325, lung cancer cell line A549, brain metastatic lung cancer cell line BT72 and prostate cancer cell line IB-4 were used to determine the killing of cancer cells by 2-bromo-isovanillin for 24 hrs. Specifically, ten groups were formed according to the type of the cancer cells. The cancer cells were diluted as appropriate, and were respectively plated into Petri dishes with a diameter of 60 cm, the amount of the cells adjusted depending on the concentration of 2-bromo-isovanillin to be added. Once adherence was achieved, each cell type received dosages of 5, 10, 20 and 40 μmol/L in triplicates. After 24 hrs of continuous action, the medium was replaced by a drug-free DMEM liquid medium. The cells were cultured for a total of 2 weeks. At the end of the culturing period, the cells were fixed and subjected to Giemsa staining. Then the cell clones were counted. The experimental data were expressed as the mean of 24 experiments and were plotted as a growth curve of cancer cells, as shown in FIG. 3. The results indicated that 2-bromo-isovanillin had significant inhibitory effect on the proliferation of all ten cancer cell lines of different tissue origins.

Figure 4A:
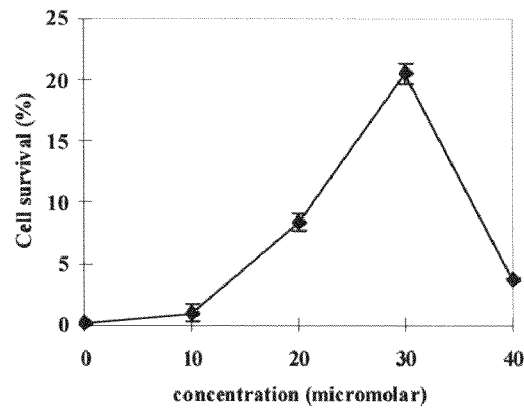
FIG. 4A shows the dose-effect relationship of 2-bromo-isovanillin induced apoptosis in leukemia cell line Jurkat.
Figure 4B:
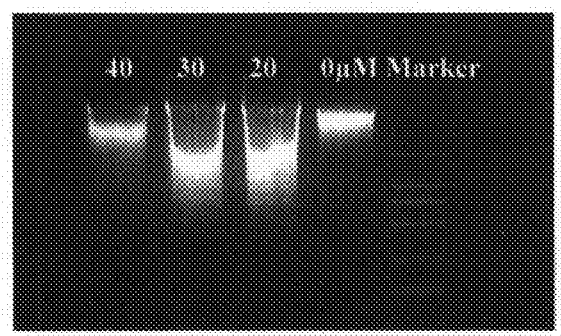
FIG. 4B shows the results of gel electrophoresis of DNA from leukemia cell line Jurkat subjected to 2-bromo-isovanillin.
Figure 4C:
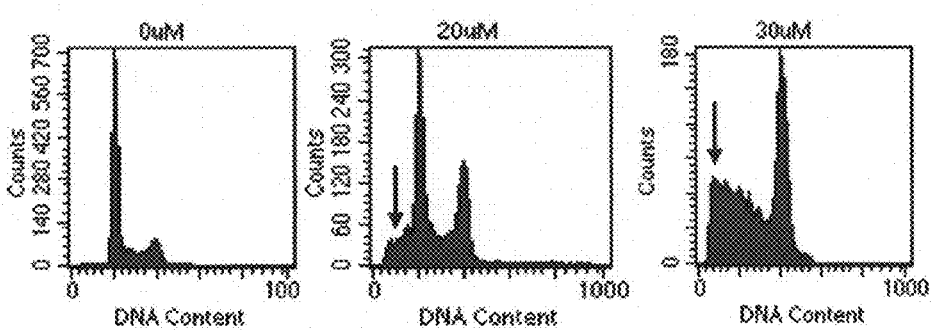
FIG. 4C shows the flow cytometry results of leukemia cell line Jurkat subjected to 2-bromo-isovanillin.

3. Using the same procedure as described under items 1 and 2, the leukemia cells Jurkat were diluted, and plated into Petri dishes with a diameter of 60 cm, the amount of the cells adjusted depending on the concentration of 2-bromo-isovanillin to be added. Once adherence was achieved, the cells received dosages of 0, 10, 20, 30 and 40 μmol/L in triplicates. After 24 hrs of continuous action, the medium was replaced by a drug-free 1640 medium supplemented with 10% newborn calf serum. The cells were cultured for a total of 2 weeks. At the end of the culturing period, the cells were subjected to Hoechst 33258 and FDA double fluorescence staining and the results were plotted as an apoptosis curve, as shown in FIG. 4A. It revealed the dose-effect relationship of 2-bromo-isovanillin induced apoptosis in Jurkat cells as measured by Hoechst 33258 and FDA double fluorescence staining technique, wherein a dose of 40 μmol/L or above could induced necrosis or M phase catastrophic death in cancer cells. DNA was extracted from the cancer cells, and a 2% agarose gel electrophoresis revealed DNA fragmentation bands characteristic of apoptosis, as shown in FIG. 4B (lane Marker: DNA molecular weight standards; lanes 0, 20, 30, 40 respectively represent DNA from leukemia cells Jurkat subjected to 0, 20, 30, 40 μmol/L 2-bromo-isovanillin). Further, flow cytometry was used to detect cell apoptosis, and the results are shown in FIG. 4C (0, 20, 30 μM respectively represent the results of cell apoptosis of the cancer cells subjected to 0, 20, 30 μmol/L 2-bromo-isovanillin, and the apoptosis peak was marked with an arrow), indicating that 2-bromo-isovanillin significantly induced apoptosis in leukemia cell line Jurkat.

Example 3

Determination of the Radiosensitizing Activity of 2-bromo-isovanillin

By way of example, human cervical cancer cell line HeLa was used to determine the radiosensitizing activity of 2-bromo-isovanillin.

Figure 5:
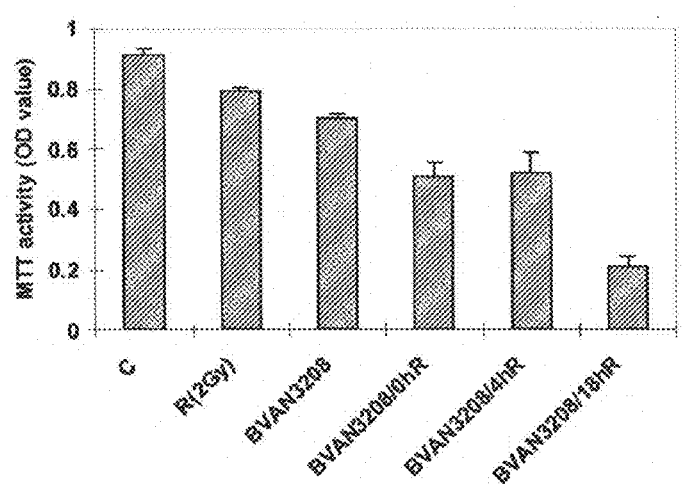
FIG. 5 shows the results of the inhibitory effect of 2-bromo-isovanillin in combination with 2 Gy Co-60 γ radiation on the proliferation of human cervical cancer cell line HeLa.

Specifically, human cervical cancer cells HeLa were divided into six groups, diluted as appropriate, and plated into Petri dishes with a diameter of 60 cm. The amount of cells plated in each Petri dish was 300/500 for 0 Gy group (without Co-60 γ radiation), or 400/800 for 2 Gy group. Once adherence was achieved, three groups were treated with 20 µmol/L 2-bromo-isovanillin (BVAN3208) for 0, 4 and 18 hrs, respectively and then irradiated with Co-60 γ ray at 2 Gy, followed by two weeks under conventional culturing conditions. As to the other three groups, one group was treated with 20 µmol/L 2-bromo-isovanillin (BVAN3208) for 72 hrs and then cultured for two weeks under conventional conditions, one group received irradiation with Co-60 γ ray at 2 Gy and then was cultured for two weeks under conventional conditions, and the remaining group as control received no treatment at all and was cultured for two weeks under conventional conditions. 48 hrs after irradiation with Co-60 γ ray, using MTT assay, the optical density (OD) values at 490 nm were measured and recorded, wherein the magnitude of OD value is indicative of cell number, i.e., cell proliferation. The results are shown in FIG. 5, wherein C represents the control group, R(2 Gy) represents the group treated with Co-60 γ ray alone, BVAN3208 represents the group treated with 20 µmol/L 2-bromo-isovanillin alone, and BVAN3208/0 h R, BVAN3208/4 h R and BVAN3208/18 h R respectively represent the groups treated with 20 µmol/L 2-bromo-isovanillin for 0, 4, 18 hrs before irradiation with Co-60 γ ray. The survival rates of the cancer cells treated with 2 Gy Co-60 γ ray radiation or 20 µmol/L 2-bromo-isovanillin for 72 hrs were 76% and 70%, respectively. The pretreatment of the cancer cells with 20 µmol/L 2-bromo-isovanillin for 0, 4, 18 hrs before radiation reduced the cell survival rate to about 51% (radiation immediately or 4 hrs after administration) and 21% (radiation 18 hrs after administration), indicating that pretreatment of the cancer cells with 20 µmol/L 2-bromo-isovanillin could significantly enhance the death rate of irradiated cells, and a pretreatment at 18 hrs prior to the radiation had a stronger sensitizing effect, with a sensitization ratio of 3.32.

Example 4

2-bromo-isovanillin Induced G2/M Arrest in Cancer Cells

Figure 6:
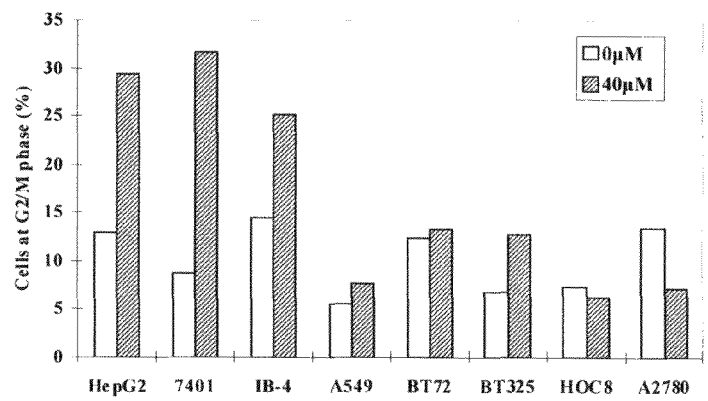
FIG. 6 shows the ratio of cells at G2/M phase in a number of cancer cell lines after 24 hrs' treatment with 2-bromo-isovanillin.

By way of example, human liver cancer cell lines HepG2 and 7402, human ovarian cancer cell lines HOC8 and A2780, human glioma cell line BT325, lung cancer cell line A549, brain metastatic lung cancer cell line BT72 and prostate cancer cell line IB-4 were used to investigate the G2/M arresting of solid tumor cells of different tissue origins by 2-bromo-isovanillin as measured by the ratio of cells at G2/M phase. Specifically, the cancer cells were divided into two groups, and were treated with 0 or 40 µmol/L 2-bromo-isovanillin for 24 hours. Then the cells were harvested and analyzed for changes in cell cycle and cell apoptosis by flow cytometry. The results of G2/M cell ratios are shown in FIG. 6. After 24 hrs of treatment with 40 µmol/L 2-bromo-isovanillin, human liver cancer cells HepG2/7402 and prostate cancer cells IB-4 were arrested at G2/M phase, yet some tumor cells did not exhibit obvious cell cycle arrest.

Figure 7A:
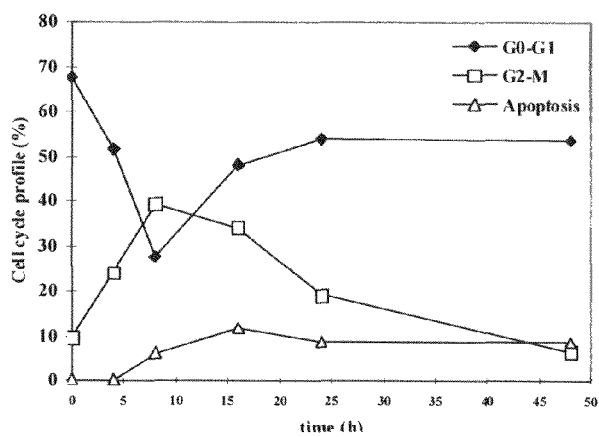
FIG. 7A shows the cell cycle profile of human liver cancer cell line HepG2 treated with 2-bromo-isovanillin for different periods of time (0-50 h)
Figure 7B:
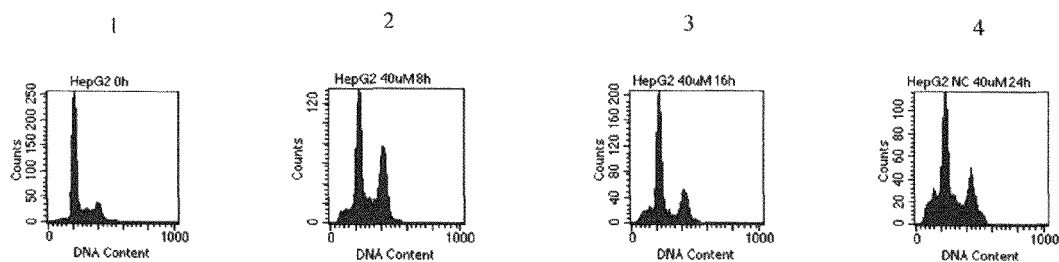
FIG. 7B shows the results of cell apoptosis in human liver cancer cell line HepG2 treated with 2-bromo-isovanillin for different periods of time (0, 8, 16, 24 h) as measured by flow cytometry.

2. In a separate experiment, the cell cycle profile and apoptosis rate of human liver cancer cell line HepG2 treated with 40 µmol/L 2-bromo-isovanillin for different periods of time (0-50 h) were studied, and the results are shown in FIGS. 7A and 7B (1, 2, 3, 4 respectively represent the apoptosis results for treatment with 40 µmol/L 2-bromo-isovanillin for 0, 8, 16, 24 hrs). It can be seen that an obvious G2/M arrest began to appear after 4 hrs of treatment with 2-bromo-isovanillin, reaching a peak at 8-16 hrs, meanwhile, cells at G0/G1 phase significantly decreased; and cell apoptosis significantly increased after 8 hrs of treatment.

Figure 8:
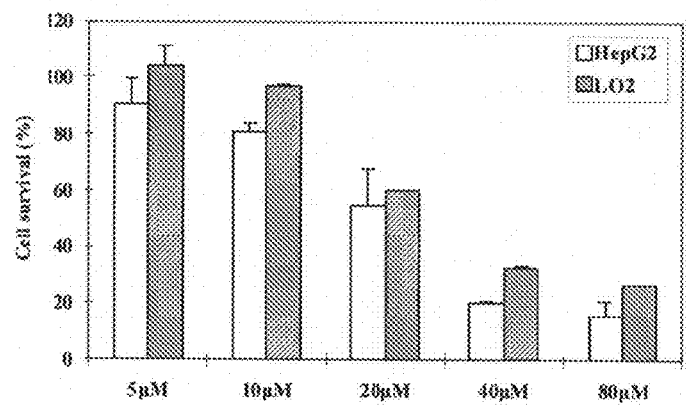
FIG. 8 shows the results of survival rates of liver cancer cell line HepG2 and normal hepatic cell line LO2 treated with different concentrations of 2-bromo-isovanillin for 24 hrs, as measured by clonogenic assay.

By way of example, human liver cancer cell line HepG2 and normal human hepatic cell line LO2 were used to study the inhibitory effect of 2-bromo-isovanillin on the growth of liver cancer cells and normal cells by clonogenic assay. Specifically, five groups were formed according to the drug concentration, and the liver cancer cells HepG2 and normal hepatic cells LO2 were respectively treated with 5, 10, 20, 40 and 80 µmol/L 2-bromo-isovanillin for 24 hrs. Then cell survival was measured by clonogenic assay (FIG. 8). In addition, the cell cycle profile and apoptotic effect were compared using flow cytometry. It resulted that the killing effect of 24 hrs of 2-bromo-isovanillin on the liver cancer cells HepG2 was significantly higher than on the normal hepatic cells. Example 4 experimentally proved that 2-bromo-isovanillin could induce G2/M arrest and cell apoptosis in HepG2 cells, whereas the same treatment with 40 µmol/L 2-bromo-isovanillin for 24 hrs did not result in G2/M arrest or significant cell apoptosis in LO2 cells, suggesting that 2-bromo-isovanillin has significantly less toxic effect on normal hepatic cells than on liver cancer cells.

Figure 9:
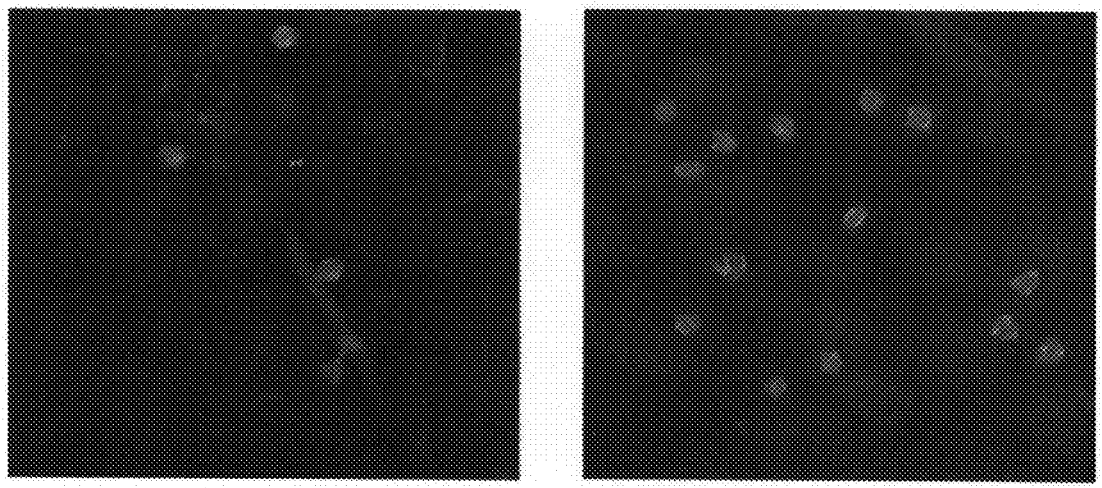
FIG. 9 shows the effect of 40 μmol/L 2-bromo-isovanillin for 24 hrs on the spindle of human liver cancer cell line HepG2, as measured by immunofluorescence in situ hybridization.

3. The experimental results from the above examples demonstrated that 2-bromo-isovanillin induced G2/M arrest in many solid tumor cell lines such as HepG2. The influence of 2-bromo-isovanillin on the spindle structure in HepG2 cells was further studied by means of in situ immunofluorescence hybridization by immunofluorescent labeling of tubulin. The results, as shown in FIG. 9, indicated that after treatment with 40 µmol/L 2-bromo-isovanillin for 24 hrs, the ratio of cells at mitotic phase significantly increased, further supporting that 2-bromo-isovanillin could induce M phase arrest. In addition, after treatment with 2-bromo-isovanillin, more than about 65% M phase cells exhibited multiple centrosomes or destroyed spindle structure, indicating that 2-bromo-isovanillin could destroy the spindle structure in cells. The cells with impaired spindle function could not undergo normal division, thereby leading to rapid cell death, i.e., mitotic catastrophe.

Example 6

Analysis of the Mechanism Underlying the Anti-Proliferative Activity of 2-bromo-isovanillin Against Cancer Cells The experimental results from the above examples demonstrated that 2-bromo-isovanillin could significantly inhibit proliferation and induce apoptosis in various cancer cells of multiple tissue origins. Moreover, treatment with 2-bromo-isovanillin for different periods of time (0-18 hrs) prior to irradiation produced different radio-sensitizing effects, suggesting that such effect was not resulted from simple addition of these two treatments, but was due to certain inherent enhancing mechanism(s). The mechanism underlying the anti-proliferative and radio-sensitizing effects of 2-bromo-isovanillin in cancer cells was analyzed through the following experiments.

1. Inhibitory Effect of 2-Bromo-Isovanillin on the Activity of Nuclear Protein DNA-PKcs Serine/Threonine Protein Kinase in Human Liver Cancer Cells HepG2

Figure 10:
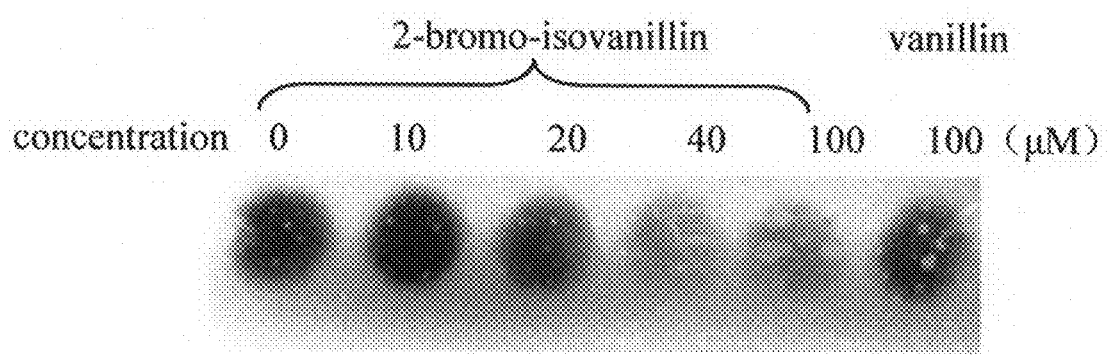
FIG. 10 shows the results of the inhibitory effect of 2-bromo-isovanillin on the kinase activity of DNA repairing proteins DNA-PKcs.

The activity of nuclear protein DNA-PKcs serine/threonine protein kinase in human liver cancer cells HepG2 treated with 0, 10, 20, 40, 100 μmol/L 2-bromo-isovanillin for 24 hrs was determined by using Sigma TECT DNA dependent protein kinase assay kit (Promega), according to the manufacturer's instructions, and the treatment with 100 μmol/L vanillin for the same period of time served as control. Basically, the assay was carried out by immobilizing the phosphorylation substrate specific to DNA-PKcs, i.e., a peptide derived from p53 protein onto a cellulose membrane, adding nuclear proteins to the solid phase reaction system, isotopically labeling the substrate by phosphorylation using $\gamma$-$^{32}$P ATP, removing non-specific signals after the isotope labeling, and visualizing the kinase activity upon X-ray film developing. The results, as illustrated in FIG. 10, showed that 20 μmol/L 2-bromo-isovanillin significantly inhibited the activity of the nuclear protein DNA-PKcs serine/threonine protein kinase in cancer cells, and such inhibitory effect was more remarkable with 40-100 μmol/L 2-bromo-isovanillin. In contrast, vanillin was significantly weaker in terms of inhibitory effect on the activity of nuclear protein DNA-PKcs serine/threonine protein kinase in cancer cells.

Figure 11:
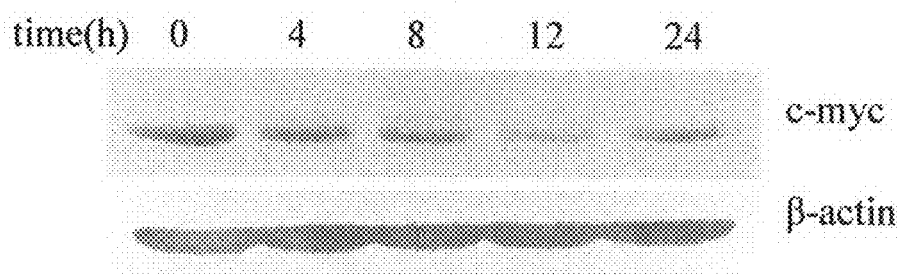
FIG. 11 shows the Western blotting results of degradation of oncogene c-myc protein promoted by 2-bromo-isovanillin in liver cancer cells

2. Determination of the Level of c-Myc Protein Expression in Tumor Cells Treated with 2-Bromo-Isovanillin by Western Immunoblotting The expression level of c-myc protein in human cervical cancer cell line HeLa treated with 2-bromo-isovanillin was determined by Western immunoblotting. In the Western blotting, the mouse anti-human c-myc protein monoclonal antibody SC-40 (purchased from Santa Cruz) was used as the primary antibody, and the goat anti-mouse antibody IgG-HRP (purchased from Zhongshan Reagent Co.) was used as the secondary antibody. Total proteins from human cervical cancer cells HeLa treated with 40 μmol/L 2-bromo-isovanillin for 0, 4, 8, 12, 24 hrs were extracted according to conventional methods, quantified and subjected to SDS-PAGE electrophoresis, followed by transferring to a membrane and immunoblotting, using β-actin as control. The results of Western immunoblotting, as shown in FIG. 11 (lanes 0, 4, 8, 12, 24 respectively represent the expression level of c-myc protein in HeLa cells treated with 40 μmol/L 2-bromo-isovanillin for 0, 4, 8, 12, 24 hrs), revealed that the expression level of c-myc protein in tumor cells treated with 40 μmol/L 2-bromo-isovanillin decreased, and the decrease became even more remarkable as the treating time increased. It is known that normally c-myc protein has a short half life of only 10-30 min, whereas in many tumor cells, the stability of c-myc protein significantly increases, leading to over-expression. It was demonstrated that 2-bromo-isovanillin could reduce the stability of c-myc protein in tumor cells, and facilitate the degradation of c-myc protein.

The invention claimed is:

1. A pharmaceutical composition for the treatment of cancer and/or for radio- and chemotherapy sensitization, which comprises an effective amount of 2-bromo-isovanillin.

2. The pharmaceutical composition according to claim 1, which is in the form of capsules, tablets, powders, granules, oral solutions or injections.

* * * * *